United States Patent [19]
Neiswander

[11] Patent Number: 5,088,203
[45] Date of Patent: Feb. 18, 1992

[54] METHOD AND APPARATUS FOR EYE GLASSES POSITION MEASUREMENT SYSTEM AND/OR FOR VERTEX MEASUREMENT SYSTEM

[76] Inventor: Leonard E. Neiswander, 1536 Parkwy., Sevierville, Tenn. 37862

[21] Appl. No.: 716,090

[22] Filed: Jun. 17, 1991

[51] Int. Cl.⁵ ............................................. A61B 3/10
[52] U.S. Cl. ...................................... 33/200; 33/512; 33/278; 351/204
[58] Field of Search .................. 33/200, 512, 262, 276, 33/278, 280, DIG. 21; 356/372, 383; 351/200, 204, 208

[56] References Cited

U.S. PATENT DOCUMENTS

| | | | |
|---|---|---|---|
| 1,621,352 | 3/1927 | Currier | 33/200 |
| 4,391,527 | 7/1983 | Hennequin | 351/204 |
| 4,653,881 | 3/1987 | Joncour | 33/200 |
| 5,007,739 | 4/1991 | Shimano et al. | 356/383 |

FOREIGN PATENT DOCUMENTS 0154132  2/1982  Fed. Rep. of Germany ...... 356/383

Primary Examiner—Allan N. Shoap
Assistant Examiner—Alvin Wirthlin
Attorney, Agent, or Firm—L. F. Hilbers

[57] ABSTRACT

An eyeglasses measuring system comprises a fixed light source which projects a light beam onto two reflecting mirrors. The reflecting mirrors split the light beam into two separate light beams. One of the beams is positioned so that it tangentially illuminates the patient's cornea. A target mirror is then moved, by turning an adjustment screw. This adjustment positions the projection path of the second light beam tangentially onto the front surface of the patient's eyeglasses. The distance between the two beams of light is then determined by reading a scale.

2 Claims, 1 Drawing Sheet

METHOD AND APPARATUS FOR EYE GLASSES POSITION MEASUREMENT SYSTEM AND/OR FOR VERTEX MEASUREMENT SYSTEM

BACKGROUND OF THE INVENTION

I. Field of the Invention

This invention relates generally to a method and apparatus for optically measuring a distance; and more particularly, to a method and apparatus for optically measuring the distance between a patient's cornea and the outer edge of his eyeglass lenses.

II. Prior Art and other Considerations

In a conventional method for determining the distance between the patient's cornea and his eyeglass lenses the distance is estimated by hand using a ruler. This method has the disadvantages of a loss of accuracy and a difficulty of use.

Another prior art method uses an inside caliper to measure the distance from the patient's cornea to the lenses of his eyeglasses. This method has the disadvantage that the caliper comes into physical contact with the patient's eyelids. This method also cannot guarantee that the distance is being measured from the proper point on the cornea.

Heretofore, an optical measuring instrument for example as the projector has been of such an arrangement that the object being measured is rested on a mount and illuminated by parallel ray beams, an image of projection of the object being measured is made to focus on a screen by a transmitted light or a reflected light of the parallel ray beams, and the dimensions, contour and the like of the object being measured. However, in general, so-called blurs are found at the edges of the image of the object being measured, which has been projected on the screen. In consequence, it is difficult to accurately read a measured value from the coincidence between the image formed on the screen and a hair line.

Another projection method employs the science of interferences. However, this method presents the disadvantage that interferences such as external irregular lights affect the performance of the projector to a great extent and the measuring accuracy is greatly deteriorated due to variations in the signal obtained from the photoelectric element and in the reference voltage.

Still another projection method uses a photoelectric element. However, this method presents the disadvantages that the position of the edge thus detected may differ depending on the value of the relative movement rates between the photoelectric element and the image of projection, and further, the measuring accuracy is greatly affected by a variation in a reference voltage.

Further, the scope of application of the illumination ray beams to light intensity is small, and a sensor portion or a circuit portion becomes complicated in construction.

Particularly, in the projector, the brightness of the image projected on the screen is varied due to the fatigue of a light source lamp for illumination, the characteristics of lenses in a projection system and the external irregular lights.

Furthermore, according to the conventional edge detecting methods, when the focus of the image of projection is shifted, the wave forms emitted from the photoelectric element or elements become gently sloped, thereby presenting the disadvantage that no accurate edge can be detected. The disadvantage is common in the edge detection among the optical measuring instruments wherein, in general, a transmitted light or a reflected light is detected to directly or indirectly measure dimensions and the like of an object being measured.

It is known in the art to provide optical measuring apparatus for measuring the diameter of large work pieces, comprising a pair of telescopic sights displaceable on a common guide and having a pair of measuring marks which can be aimed at the two end points of the diameter of the work piece. The displacement of the telescopic sights can be read on a scale, so as to indicate the length of the diameter. This measuring apparatus can be used, however, only for measuring the diameter of stationary work pieces, but cannot be used if the work piece is moving, for example rotating, because then the reference marks are removed from the aiming position.

According to another apparatus, known in the art, a light ray is emitted towards the work piece, comes into contact with the surface of the latter and is viewed in a microscope. Interference stripes are thus produced, the positions of which can be determined by means of a reference mark. Thereafter, the apparatus is displaced until the reference mark on the other end of the work piece receives the same interference strips. The displacement indicates the desired value of the diameter. This apparatus suffers from the disadvantage of being complicated and time-consuming in operation and cannot be used for effecting the measurement of work pieces having specular of semi-specular surfaces.

Still another apparatus has, in addition to a pair of telescopic sights displaceable on a guide, and a scale from which the displacement of the telescopic sights can be read, a reference mark and projecting means for projecting said reference mark in the direction of the diameter of the work piece onto the two end points of the diameter of the work piece. The reference marks as projected can be viewed with the two telescopic sights. In case of a rotating work piece and position of the two reference marks is not changed as long as the diameter remains the same. Preferably, light bands are used as reference marks and a diaphragm is provided, allowing for the variation of the respective widths and light intensities of the light bands. This is still relatively complicated and time-consuming in operation.

SUMMARY

In view of the foregoing, it is an object of the present invention to provide a method and apparatus for effectively measuring the distance between a patient's cornea and his eyeglass lenses.

An advantage of the present invention is the provision of a method and apparatus wherein the distance between a patient's cornea and eyeglass lens is quickly, easily and accurately determined.

Another advantage of the present invention is the provision of a method and apparatus wherein the measuring instrument never contacts the patient's eyeball.

Another advantage of the present invention is the provision of a method and apparatus wherein the distance is easily measured from the proper point on the patient's cornea.

An eyeglasses measuring system comprises two parallel beams of light, a means for positioning one beam to safely shine on the cornea, a means for the adjustment, as desired, of the distance between the beams, and a means measuring this distance. The position of one beam of light is aligned such that it projects onto the edge of the patient's cornea by the positioning means. The the other beam is moved by the adjustment means so that it projects onto the front surface of the patient's eyeglasses at a point coincident with the straight ahead line of sight of the patient. The measuring means is then used to determine the distance between the two beams.

BRIEF DESCRIPTION OF THE DRAWINGS

The foregoing and other objects, features, and advantages of the invention will be apparent from the following more particular description of preferred embodiments as illustrated in the accompanying drawings in which reference characters refer to the same parts throughout the various views. The drawings are not necessarily to scale, emphasis instead being placed upon illustrating the principles of the invention.

DETAILED DESCRIPTION OF THE DRAWINGS

Figure 1:
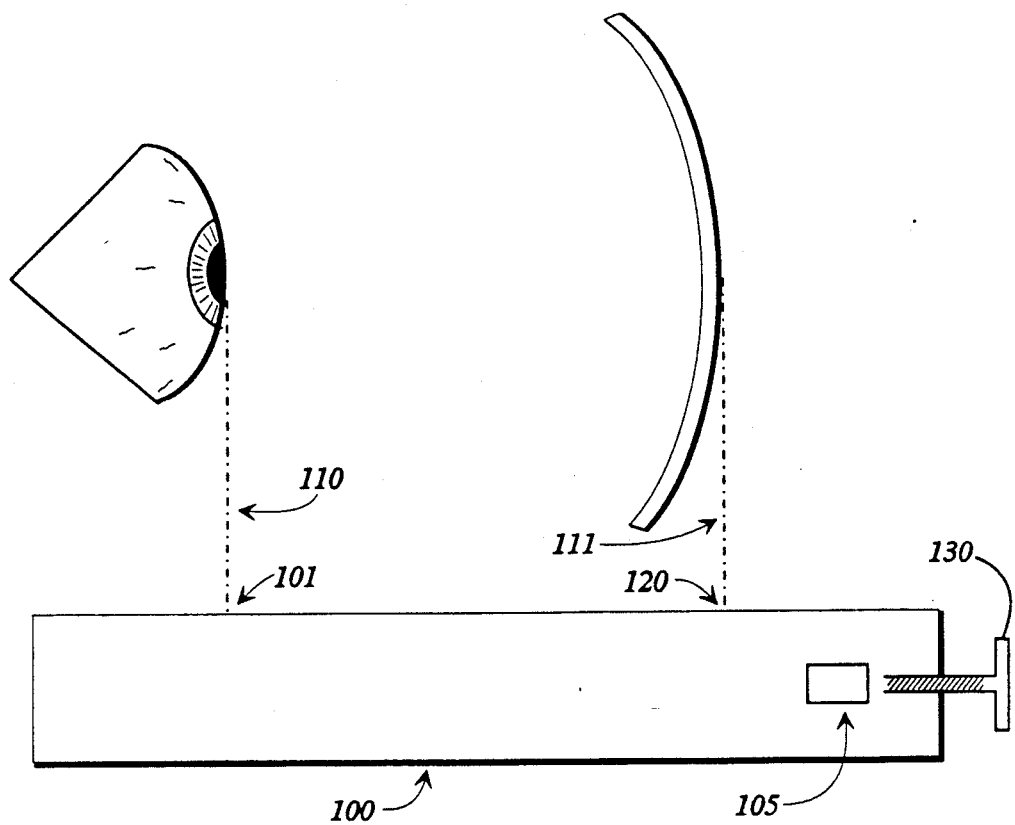
FIG. 1 is a top view of a first preferred embodiment of an eye glasses position measuring system.

The first preferred embodiment of the Eye Glasses Position Measuring System of FIG. 1 comprises a movable light source 120, an adjustment screw 130, and a housing 100. The housing 100 comprises a fixed light source 101, having a fixed source light beam 110, and either a scale 102 or a digital readout 105.

The movable light source 120, having a moving source light beam 111, is movably attached to the housing 100. The adjustment screw 130 is rotatably attached to the movable light source 120 and the housing 100. The scale 102 (see FIG. 2) is installed onto the housing 100 and between the fixed light source 101 and the movable light source 120. If the system uses a digital readout 105 the scale 102 is replaced by a digital readout 105 on the housing 100.

The fixed light source 101 projects a light beam 110 from the housing 100 perpendicular to the patient's line of sight. The movable light source 120 can be moved, parallel to the patient's line of sight, along the length of the scale 102 by turning the adjustment screw 130.

In use the fixed light source 101 is placed such that the fixed source light beam 110 illuminates the front edge of the patient's eye. The movable light source 120 is moved, by turning the adjustment screw 130, so that the moving source light beam 111 illuminates the front edge of the patient's glasses. The distance between the fixed light source 101 and the movable light source 120 is then determined from the scale 102 or the digital readout 105.

Figure 2:
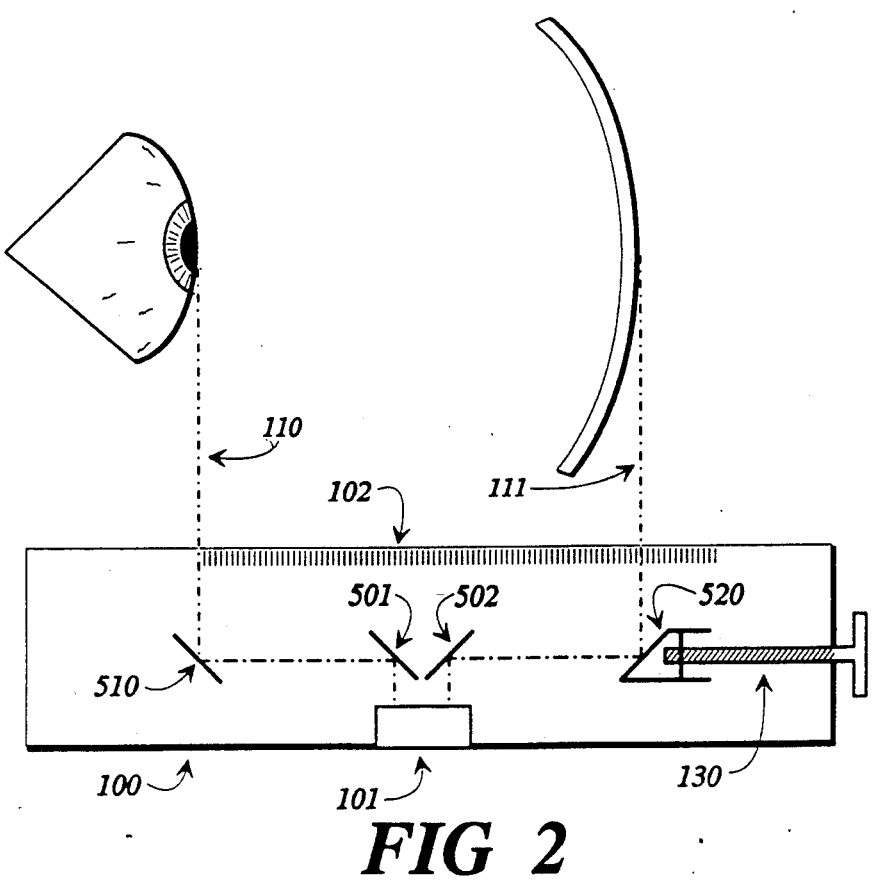
FIG. 2 is a top view of a second preferred embodiment of an eye glasses position measuring system.

The second preferred embodiment of the Eye Glasses Position Measuring System of FIG. 2 comprises a light source 101, an adjustment screw 130, and a housing 100. The housing 100 comprises a left reflecting mirror 501, a right reflecting mirror 502, a fixed mirror 510, a movable mirror 520, and a scale 102 or a digital readout 105.

The light source 101 is attached to the housing 100. The adjustment screw 130 is attached to the movable mirror 520 and the housing 100. The scale 102 is on the housing 100 and between the light beams reflected from the fixed mirror 510 and the movable mirror 520. If the system uses a digital readout 105 the scale 102 is replaced by a digital readout 105 on the housing 100.

The light source 101 projects light beams 110, 111 onto the two reflecting mirrors 501, 502. The left reflecting mirror 501 reflects the left light beam 110 onto the fixed mirror 510. The left light beam 110 reflects off the fixed mirror 510 on a line perpendicular to the patient's line of sight. The right mirror 502 reflects the right light beam 111 onto the movable mirror 520. The right light beam 110 reflects off of the movable mirror 520 in a line parallel to the light beam 110 reflected from the fixed mirror 510. The movable mirror 520 can be moved along the length of the scale 102, parallel to the patient's straight ahead line of sight, by turning the adjustment screw 130.

In use the housing 100 is placed such that the left light beam 110 from the fixed mirror 510 illuminates the front edge of the patient's cornea. The movable mirror 520 is moved, by turning the adjustment screw 130, so that the right light beam 111, reflected off the movable mirror 520, illuminates the front edge of the patient's glasses. The distance between the two light beams is then determined from the scale 102 or the digital readout 105.

While the invention has been particularly shown and described with reference to the preferred embodiments thereof, it will be understood by those skilled in the art that various alterations in form and detail may be made therein without departing from the spirit and scope on the invention.

The embodiments of the invention in which an exclusive property or privilege is claimed are defined as follows:

1. An apparatus for taking measurements of the dimensioning of eyeglasses, said apparatus comprising:
    a housing;
    means for producing a first light beam a point of which is coincident with the cornea of a patient's eyeball, said means contained within the housing;
    means for producing a second light beam a point of which is coincident with the respective lens of the patient's eyeglasses;
    means for adjusting the position of the two beams with respect to each other and to the patient; and
    means for measuring the distance between the two points.

2. A method of taking measurements of the dimensioning of eyeglasses, said method comprising the steps of:
    projecting a first light beam onto a point on the cornea of a patient's eyeball,
    adjusting a second light beam with respect to said first light beam to project onto a point on the respective lens of the patient's eyeglasses; and
    measuring the distance between the two points.

* * * * *